(12) United States Patent
Carrington

(10) Patent No.: US 7,410,612 B1
(45) Date of Patent: Aug. 12, 2008

(54) GUNPOWDER PARTICLE TEST KIT

(76) Inventor: John H. Carrington, 2316 Wakefield Plantation Rd., Raleigh, NC (US) 27614

( * ) Notice: Subject to any disclaimer, the term of this patent is extended or adjusted under 35 U.S.C. 154(b) by 1014 days.

(21) Appl. No.: 10/727,397

(22) Filed: Dec. 4, 2003

(51) Int. Cl.
G01N 31/22 (2006.01)
G01N 33/22 (2006.01)

(52) U.S. Cl. .......................... 422/61; 422/55; 422/68.1; 436/110; 436/165; 436/808; 436/810

(58) Field of Classification Search .................. 422/55, 422/61, 68.1; 436/110, 165, 808, 810
See application file for complete search history.

(56) References Cited

U.S. PATENT DOCUMENTS 5,709,838 A * 1/1998 Porter et al. .................. 422/61

6,613,576 B1 * 9/2003 Rodacy et al. .............. 436/164

* cited by examiner

Primary Examiner—Jill Warden
Assistant Examiner—Paul S Hyun
(74) Attorney, Agent, or Firm—Ishman Law Firm P.C.

(57) ABSTRACT

A gunpowder particle test kit for determining gunpowder residue includes a transparent sleeve having a closed end and an open folded end sealed with a clip forming a sealed cavity carrying a test strip and a crushable ampoule carrying a diphenylamine solution. The test strip has an adhesive area on a front surface. An opaque label is provided on a rear surface on the sleeve opposite the adhesive area. In use, the clip is removed to open the cavity, the test strip removed and applied to possible residue areas on a subject. The strip is returned to the cavity; the clip reapplied to seal the cavity. Thereafter, the ampoule is crushed to release the solution, which develops a distinctive coloration observable against the label to indicate the presence of possible gunpowder residue.

10 Claims, 4 Drawing Sheets

FIG. 6
FIG. 7
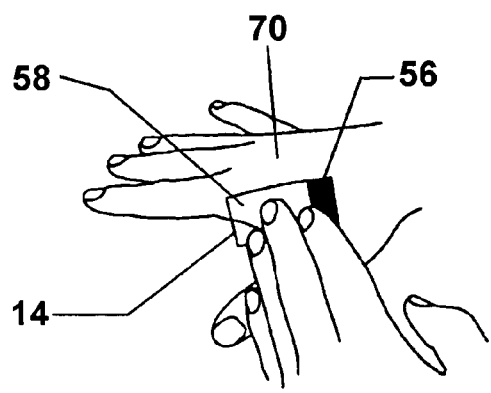
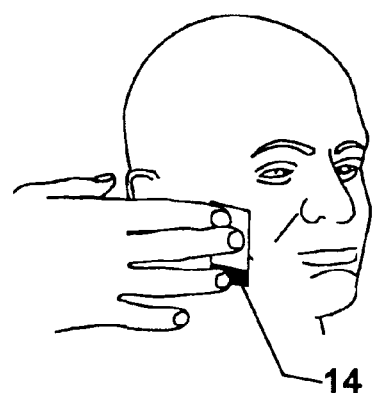
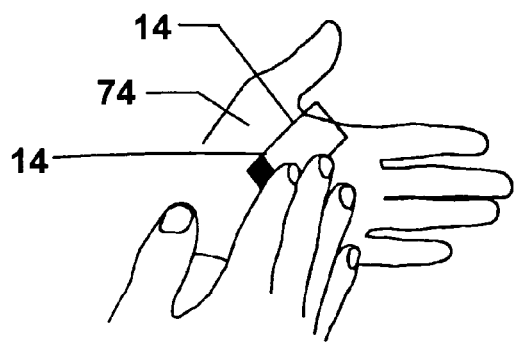
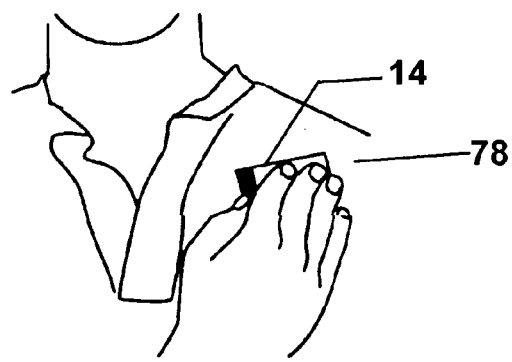
FIG. 8
FIG. 9

GUNPOWDER PARTICLE TEST KIT

FIELD OF THE INVENTION

The present invention relates to test kits for detecting compounds associated with explosives and, in particular, a test kit for gunpowder residue that can be used on site for the determination of gunpowder particulates on a subject.

BACKGROUND OF THE INVENTION

The rapid identification of key suspects is an important aspect of a crime investigation. The crime scene requires that the law enforcement officers rapidly separate suspects from witnesses. When a shooting is involved, the officers must identify the shooter and eliminate others. Gunpowder residue contains characteristic particulates, morphological and elemental, that can be identified at forensics laboratories by sophisticated equipment and analysis. The laboratories are remotely located and heavily contracted, and days might elapse before determinations can be made, obviously hampering the ability to solve the shooting.

One of the first tests for more rapidly identifying and eliminating potential suspects in a shooting incident involved melted paraffin that was poured on a suspect's hands and allowed to harden. Thereafter, the cast was removed and sprayed with a chemical solution to identify residue. These tests convert nitrocellulose and nitroglycerine into nitrates, presumptively associated with gunpowder residue, that develop distinctive coloration in the solution. The tests could be performed locally but not conveniently in the field. Later, chemical tests were developed for trace elements in gunpowder residue, i.e. antimony, lead and barium. These elements are not commonly found in nature, reducing extraneous nitrate presence, and changed to a distinctive color in the presence of a developing solution. These test were also laboratory based and resulted in delays between testing and identification. While the foregoing provided useful in ultimately determining the shooter from a group of subjects, valuable time was lost in the investigation.

Scanning electron microscopes have also been used to provide greater certainty in the identification process and for use as probative evidence, but the expense of the equipment and specialized personnel place the test beyond the means of most law enforcement agencies for screening purposes, and where used for screening added considerable time to the identification process, thereby limiting their usefulness in most investigations.

To enable investigators to make gunpowder residue determinations in the field for presumptive screening, a number of kits are available using chemical reagents. After swabs or patches have removed residues from the subjects, the reagents are poured from containers onto the swabs and patches. After a short period, the gunpowder residues take on a distinctive coloration, indicating the presumptive presence of gunpowder particulates. Accepted reagents have included diphenylamine and sodium rhodizonate. These field tests, while enabling field personnel to quickly screen plural subjects for presumptive evidence, require exposure to the chemical reagents. The reagents generally contain concentrated acids that can be hazardous if improperly handled, causing skin burn on contact and degradation of organic material including clothing. Moreover, the disposal of the chemicals and test supplies also presents problems. It has accordingly been deemed desirable in the law enforcement field to provide a field test kit for the screening of potential suspects for gunpowder residues that is safe, quick, accurate and inexpensive to use by ordinary law enforcement personnel.

SUMMARY OF THE INVENTION

The present invention provides a field test kit for gunpowder particles that enables the investigators to remove particulate matter from a subject and test for gunpowder residue in an on-site sealed environment without exposure to hazardous chemicals. The kit includes only four components: a transparent flexible plastic pouch having a cavity sealed by a retaining clip and carrying a lift strip for removing residues, and a reagent ampoule containing a diphenylamine solution for detecting gunpowder residues with a characteristic color change. The pouch includes an opaque label for enhancing color differentiation. For testing, the clip is removed and the lift strip withdrawn. The strip includes an adhesive layer covered by a removable protective strip. The protective strip is removed to expose the adhesive layer, which is then applied to target areas on a subject likely to bear gunpowder residue. After collection the strip is returned to the pouch and the clip reapplied to seal the cavity. Thereafter, the ampoule is crushed exposing the strip to the reagent solution and effecting the indicative color change within minutes if residue is present which is readily discernible against the background of the label. The results and other information may be entered on the label, photographed for records, and the consumed test unit safely disposed without personnel contacting hazardous chemical. Positive test strips may undergo further analysis by forensics laboratories for possible use as probative evidence. The test kit is also useful in the identification of nitrogen containing explosive compounds, before or after detonation. Therein, the lift strips may be applied to surfaces surrounding suspects, containers and surroundings to screen for traces of an explosive mixture.

Accordingly, it is an object of the present invention to provide a test that can be quickly administered in the field by ordinary personnel to detect nitrogen compounds associated with gunpowder residue and explosives.

Another object is to provide a gunpowder residue test kit enabling field personnel to detect residues without exposure to hazardous chemicals.

A further object is to provide a kit for testing subjects for explosive particulates that contains all components for the test in a single package.

DESCRIPTION OF THE DRAWINGS

The above and other objects and advantages of the present invention will become apparent upon reading the following detailed description taken in conjunction with the accompanying drawings in which:

FIGS. 6 through 9 are illustrations of lifting strip applied to different areas of a subject for removing gunpowder particles for determination in the test kit.

DETAILED DESCRIPTION OF THE PREFERRED EMBODIMENT

Figure 1:
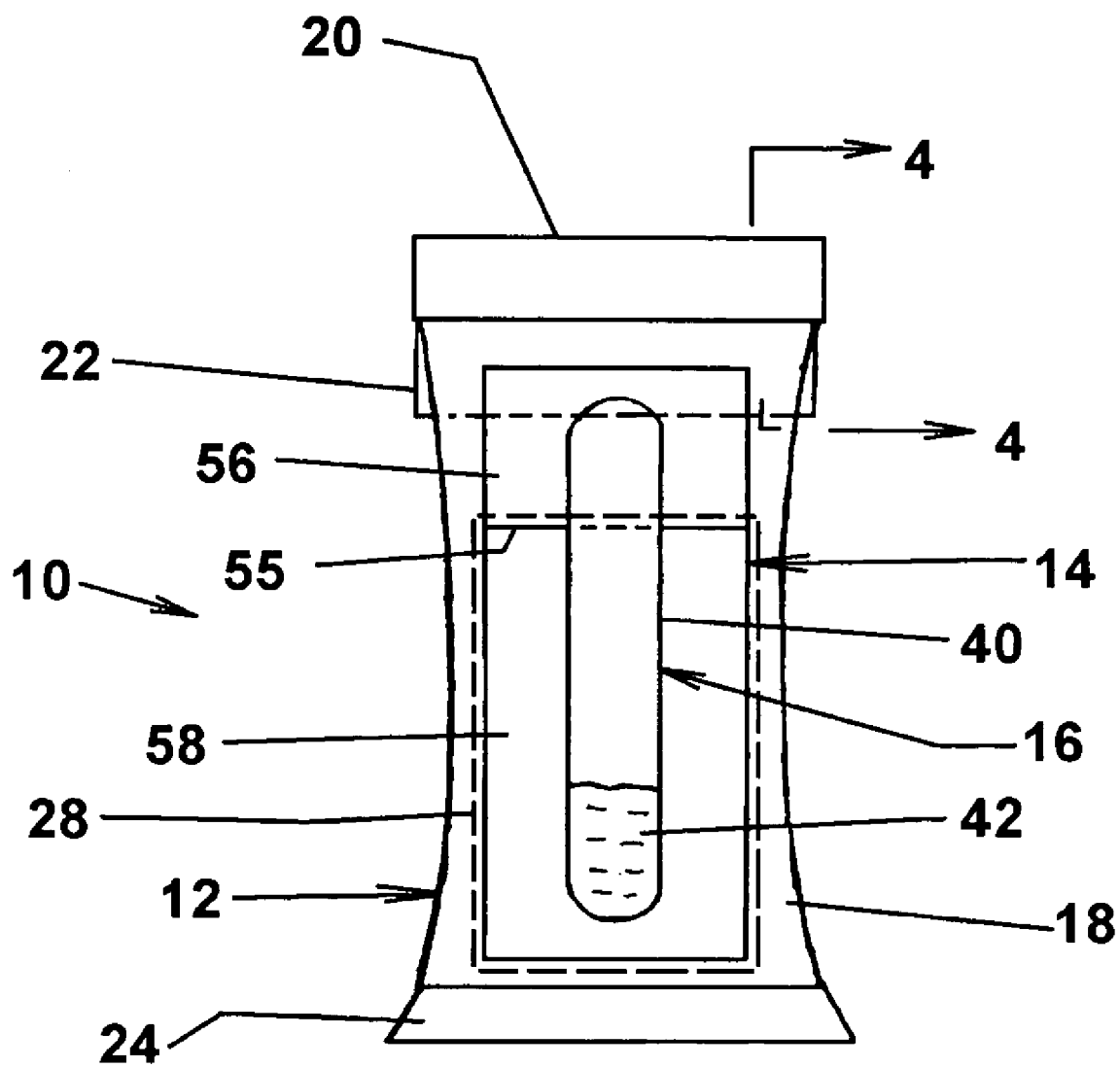
FIG. 1 is a front view of a gunpowder particle test kit in accordance with a preferred embodiment of the invention.

Referring to the drawings for the purpose of describing the preferred embodiments only and not for limiting same, FIG. 1 shows a gunpowder particle test kit 10 for on-site contemporaneous determination of the presence of gunpowder particulates from investigation surfaces, generally the hands, face and clothing of a subject. The test kit 10 comprises a clear view collector pouch 12 having a lift strip 14 and a reagent ampoule 16 carried in an interior cavity 18, and a retaining clip 20 received over the folded upper end 22 of the pouch 12 to seal the cavity.

Figure 2:
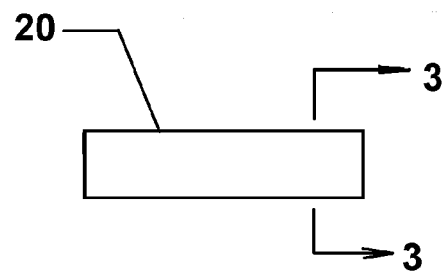
FIG. 2 is a front view of the collector pouch and retaining clip of the test kit shown in FIG. 1.
Figure 2:
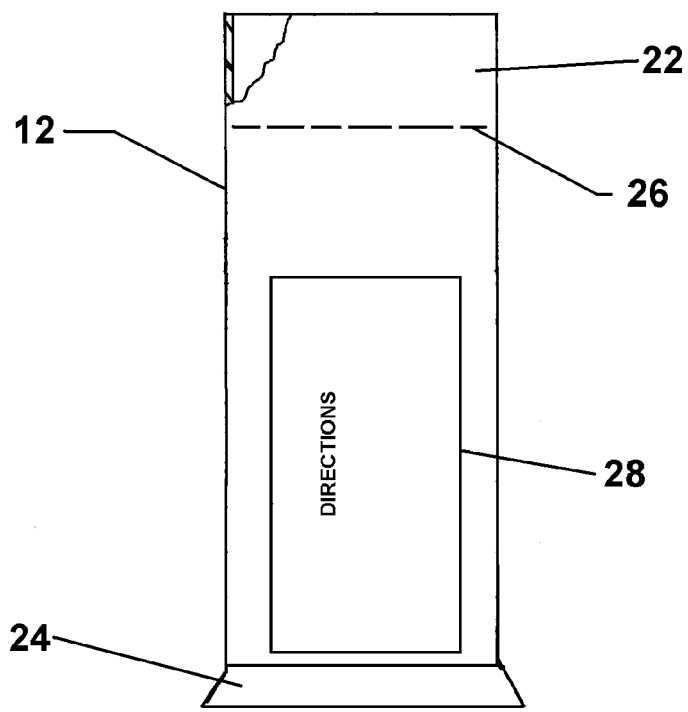
Figure 3:
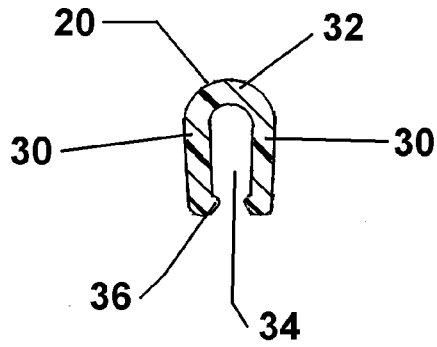
FIG. 3 is a sectioned side view of the retaining clip taken along line 3-3 in FIG. 2.
Figure 4:
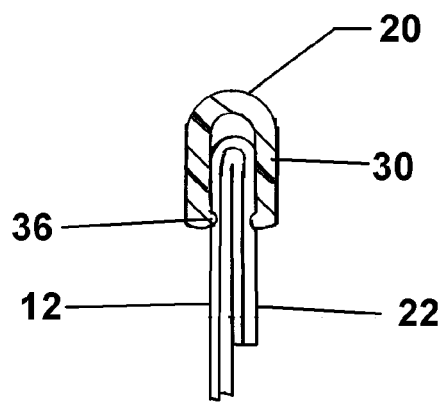
FIG. 4 is a fragmentary cross sectional view taken along line 4-4 of FIG. 1 showing the retention clip sealing the folded upper end of the collector pouch.

Referring additionally to FIGS. 2 through 4, the collector pouch 12 comprises a transparent thermoplastic tubular sleeve having a diametral heat seal 24 with the open upper end 22. The pouch 12 is flexible and the material resistant to degradation by the reactants in the ampoule 16. The material permits the upper end to be transversely folded along fold line 26 and sealed by the clip 20. An opaque adhesive label 28 is applied on one exterior sidewall of the pouch opposite the lift strip 14. The label 28 has an interior surface providing a clearly contrasting background to detected particulates and a printed or writable exterior surface containing use instructions or providing space for entering information relative to the test. Alternatively, the label 28 may be provided as an insert in the cavity or as a contrasting side surface on the lift strip. A preferred material for the pouch 14 is transparent high density polyethylene. Suitable pouches and clips for the present invention are similar to those employed in NARK II reagent kits from Sirche Fingerprint Laboratories of Youngsville, N.C.

Referring to FIGS. 3 and 4, the clip 20 is a U-shaped plastic extrusion having a pair of laterally spaced legs 30 depending from a rounded base 32 and defining therebetween a downwardly opening slot 34. Inwardly projecting longitudinal barbs 36 are formed at the lower interior surfaces of the legs 30. As shown in FIG. 4, in the sealed condition, the upper end 22 is folded over the sleeve 12 about fold line 26, and the clip legs 30 pressed thereover whereat the barbs 36 compressively engage the opposed surfaces to maintain the clip position. The clip 20 may be removed by longitudinally sliding off the folded end or by vertical removal thereof.

The ampoule 16, as shown in FIG. 1, comprises a thin wall glass ampoule body 40 containing a measured amount of a diphenylamine solution 42. The ampoule body 40 is crushable to release the solution 42. The solution 42 comprises a conventional mixture of diphenylamine, distilled water, and sulfuric acid.

Figure 10:
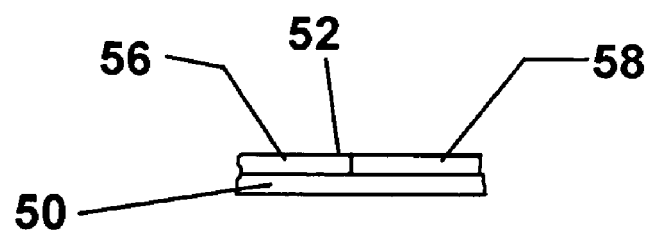
FIG. 10 is a fragmentary cross sectional view of the lift strip.

Referring to FIGS. 1 and 10, the lift strip 14 is a rectangular body having a transparent base layer 50 coated with an adhesive layer and overlaid on the top surface by a removable top layer 52. The top layer 52 is transversely scored along line 55 to establish an upper panel 56 and a lower panel 58. As described below, the lower panel 58 is removed and the exposed adhesive layer used for lifting residues from investigation surfaces. A preferred base layer 50 is a smooth, super clear polyester of around 2 mil. thickness. A suitable material is available is FLEXmark 200 poly SC-6 release liner from FLEXcon of Spencer, Mass. A suitable adhesive is a removable pressure sensitive acrylic adhesive available as FLEXmark V-58 adhesive, also available from FLEXcom.

In kit assembly, the pouch 12 with the sealed end 24 and the clip 20 in place establishes a thin walled rectangular cavity that allows the strip to maintain a generally planar profile. Preferably, the kit 10 is packaged in multiple units in a carrying case allowing ready transport to scenes wherein one or more gunpowder test determinations may be required. Individual test kits may be conveniently carried by field personnel.

Where an investigation surface, such as a subject, is identified for testing, the operator removes the clip 20 from the pouch 20, unfolds the upper end, and removes the lift strip 16. The operator grips the lifting strip 16 at the top panel 56, and removes the bottom panel 58 thus exposing the adhesive layer. Referring to FIGS. 6 through 9, for determining gunpowder residue from a subject involving a handgun, gripping the top panel, to avoid cross contamination, the adhesive panel is pressed against exposed surface areas potentially bearing GPR, such as the back of the hand 72 (FIG. 6), or the palm 74 (FIG. 8). For rifle and semi-automatic munitions, the cheek 76 (FIG. 9), and the shoulder/chest area 78 would be preferred areas for detection, as well as any other areas deemed relevant.

Figure 5:
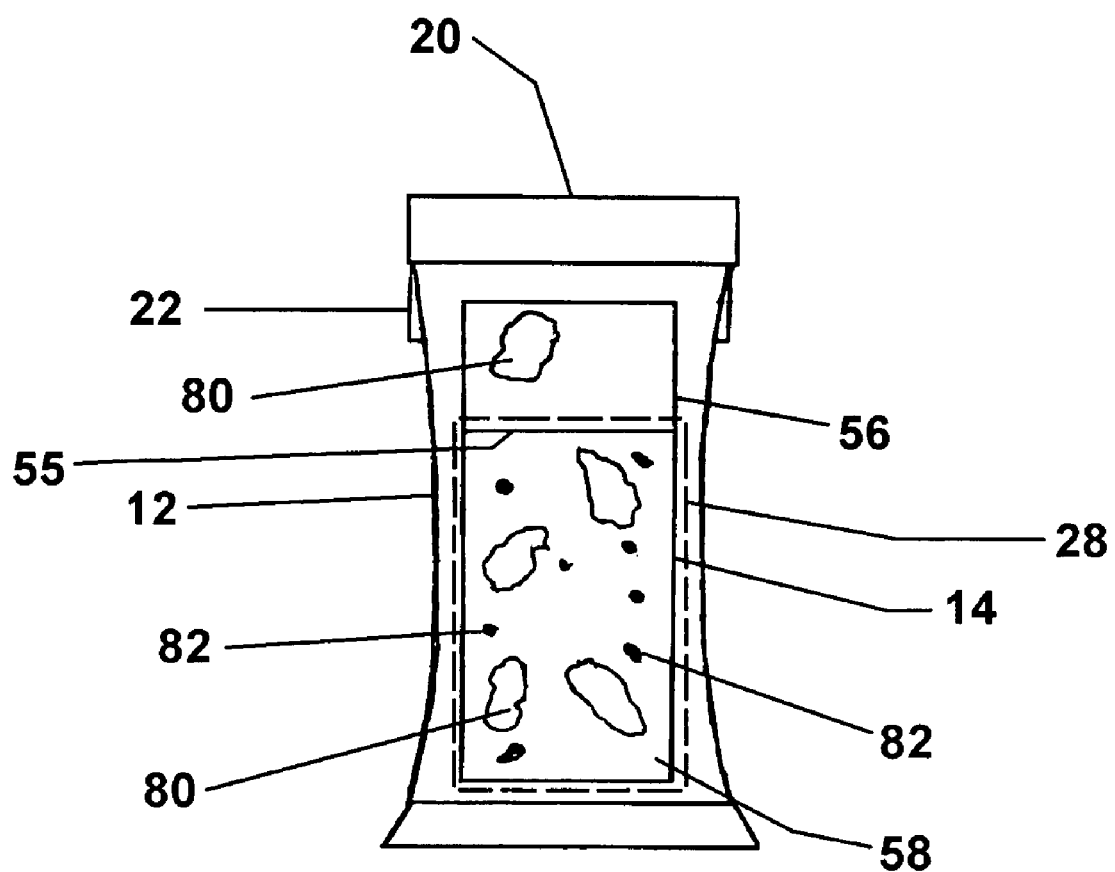
FIG. 5 is a front view of the gunpowder particle test kit of FIG. 1 illustrating breakage of the ampoule and indication of gunpowder particles.

After collection, the ampoule 16 is removed and placed on the adhesive layer, and the lift strip 14 and the ampoule 16 returned to the pouch cavity. If desired, the ampoule may remain in the cavity, and the lift strip inserted with the adhesive layer facing the ampoule to ensure reagent contact. The end of the pouch is folded and the clip 20 applied to seal the cavity. Thereafter, the operator grasps opposed surfaces of the pouch 12 with the ampoule 16 gripped between the thumb and forefinger. Referring to FIG. 5, the ampoule is squeezed until the body shatters into shards 80 releasing the reagent solution. The pouch 12 is shaken to insure wetting of the strip surfaces. If gunpowder particles, in the form of nitrate residue is present, the particles will appear as characteristic blue specks 82 on the lower panel, and be readily observable against the white background of the label 28. The color remains for a period of time during which photographs may be taken or observations recorded for securing a permanent record.

The test kit is also a fast, reliable field test for detecting trace nitrates found in over 85% of all explosives. The kit provides a first line of defense in determining the presence of trace nitrate-based explosive particulates in TNT, dynamite, Sentex, RDX and ammonium nitrates. The test kit may be used at security checkpoints, utilities, government installation, and other places with heightened security risks to screen suspects, vehicles, containers and other surfaces of interest to prevent or detect explosive events. Therein, the kit is used as described above with the lift strip adhesive applied to suspect surfaces, the lift strip sealed in the pouch, the ampoule crushed and the presence of nitrates detected by the characteristic color change.

While the present embodiment has been described with reference to the preferred embodiments, other modifications and changes thereto will become apparent. Accordingly, the invention is to be interpreted solely with reference to the following claims.

What is claimed is:

1. A test kit for the detection of nitrogen containing particulates consistent with explosive mixtures comprising: a tubular sleeve formed transparent thermoplastic flexible material, said sleeve being transversely sealed at one end and having a reverse fold at the other end to form a sealed thin walled generally rectangular cavity in said sleeve; a generally rectangular planar test strip including a base layer having an adhesive layer one surface, said test strip including a peelable layer overlying said adhesive layer, said peelable layer having a transverse score line separating said peelable layer into a first panel and a second panel, said second panel being removable to permit application of said adhesive layer against surfaces suspected of having said particles of nitrogen containing compounds thereon; an opaque substrate disposed opposite said test strip in assembly, said opaque substrate having a coloration providing clear contrast to bluish coloration, a crushable elongate glass ampoule in said cavity containing a reagent solution of diphenylamine of sulfuric acid; and a U-shaped clip having spaced resilient legs engaging said folded end whereby crushing said ampoule in said cavity will release said reagent solution onto said test strip and cause a blue coloration to any of said particles on said adhesive layer after removal of said second panel, said blue coloration being clearly visible through said sleeve against said opaque substrate.

2. The test kit as recited in claim 1 wherein said sleeve is formed of a transparent high density polyethylene.

3. The test kit as recited in claim 2 wherein said opaque substrate is an adhesive label attached to an outer surface of said sleeve opposite said adhesive layer.

4. The test kit as recited in claim 3 wherein said coloration of said opaque substrate is white.

5. The test kit as recited in claim 4 wherein the outwardly facing surface of said opaque substrate includes instructions for the use of the test kit.

6. A gunpowder particle test kit comprising: a tubular member formed of a transparent flexible acid resistant plastic material, a heat seal transversely applied against one end of said sleeve to form a closure thereat; said tubular member being reversely folded at the other end with the inner surfaces of the sleeve forming an internal test cavity; a generally U-shaped retaining clip having a pair of spaced legs compressively engaging said folded upper end to establish a closure thereat; a rectangular planar test strip in said cavity, said test strip being formed of a smooth transparent polyester film and having a pressure sensitive acrylic adhesive layer on a rectangular wall; an opaque label on an exterior surface of said tubular member opposite said adhesive layer in assembly; a removable cover layer engaging said adhesive layer; and a crushable ampoule in said cavity carrying a solution of diphenylamine and sulfuric acid effective for developing a distinctive coloration against said opaque label after adhering gunpowder particulates to said adhesive layer.

7. A gunpowder particle test kit comprising: a sleeve formed from clear flexible material having an internal cavity formed by sealed lower end and a reversely folded upper end; a retaining clip compressively engaging said folded upper end; a test strip in said cavity having a base layer including an adhesive area on a front surface; a removable cover layer engaging said adhesive area; a label on the exterior surface of said sleeve opposite said test strip; and a crushable ampoule in said cavity carrying a solution of diphenylamine and sulfuric acid effective for changing coloration after contacting gunpowder particulates at said adhesive area.

8. A method of contemporaneous onsite determination of gunpowder particulate at an investigation area, said method comprising the steps of: providing a flexible container of transparent material having an inner cavity with a open end; providing closure means for closing said open end of said container; inserting into said cavity a test strip and a crushable reagent ampoule containing a diphenylamine solution providing a distinctive coloration upon contacting gunpowder residue; providing said test strip with an adhesive area; covering said adhesive area with a removable protective layer; determining an investigation area; removing said closure means from said container; withdrawing said test strip from said cavity; removing said protective layer to expose said adhesive area; applying said adhesive area to selected areas of said investigation area; returning said test strip after said applying to said cavity; attaching said retaining means at said open end to seal said cavity; crushing said ampoule to release said solution into said cavity and onto said adhesive layer; placing an opaque surface behind said adhesive layer; and visually determining a presence of a distinctive coloration on said adhesive layer in contrast with said opaque surface indicative of gunpowder residue removed from said investigation area.

9. The method as recited in claim 8 wherein said opaque surface is provided on the exterior of said container.

10. The method as recited in claim 8 including the steps of removing said ampoule from said cavity and placing said ampoule on said adhesive layer prior to returning said test strip to said cavity.

* * * * *